US008425467B1

(12) United States Patent
Haak

(10) Patent No.: US 8,425,467 B1
(45) Date of Patent: Apr. 23, 2013

(54) CATHETER TUBE ANCHORING DEVICE

(76) Inventor: Jason D. Haak, Sioux Falls, SD (US)

( * ) Notice: Subject to any disclaimer, the term of this patent is extended or adjusted under 35 U.S.C. 154(b) by 169 days.

(21) Appl. No.: 12/855,552

(22) Filed: Aug. 12, 2010

Related U.S. Application Data

(63) Continuation-in-part of application No. 12/102,139, filed on Apr. 14, 2008, now abandoned.

(51) Int. Cl.
*A61M 5/32* (2006.01)
(52) U.S. Cl.
USPC .......................................... 604/180; 604/174
(58) Field of Classification Search .......... 604/174–180; 606/213
See application file for complete search history.

(56) References Cited

U.S. PATENT DOCUMENTS

| | | | |
|---|---|---|---|
| 3,826,254 A | 7/1974 | Mellor | |
| 3,834,380 A | 9/1974 | Boyd | |
| 4,165,748 A | 8/1979 | Johnson | |
| 5,702,371 A | 12/1997 | Bierman | |
| 5,833,665 A | 11/1998 | Bootman | |
| 6,224,571 B1 | 5/2001 | Bierman | |
| 6,428,515 B1 | 8/2002 | Bierman | |
| 7,648,492 B2 | 1/2010 | Bierman | |
| 2003/0229313 A1 | 12/2003 | Bierman | |

*Primary Examiner* — Laura A Bouchelle
*Assistant Examiner* — Melissa A Snyder
(74) *Attorney, Agent, or Firm* — Jeffrey A. Proehl; Woods, Fuller, Shultz & Smith, P.C.

(57) ABSTRACT

A catheter tube anchoring device for securing a catheter to a patient's skin, having two flexible side members and a rigid cross-member therebetween to which a retainer is mounted. The retainer holds a catheter adaptor at a 3-degree angle for patient comfort. Two rigid gripping tabs secure to each retainer side are gripped gripping while advancing a needle into the patient's vein and while attaching the catheter adaptor to a I.V. tubing, for increased patient comfort, reduction of the risk in contamination and patient infection, and to more easily and quickly start an I.V. An alternative embodiment includes prism shaped tabs containing a pressure-release polymer adhesive-containing capsules which releases the polymer adhesive through mesh openings in the tabs onto an absorbent pad on a crosslmember bottom side and onto a patient's skin to secure the device thereto either alone or in combination with a second adhesive on the patient's skin.

16 Claims, 5 Drawing Sheets

CATHETER TUBE ANCHORING DEVICE

I claim benefit of my U.S. Nonprovisional patent application Ser. No. 12/102,139 filed on Apr. 14, 2008 which is incorporated herein by reference.

BACKGROUND OF THE INVENTION

A variety of catheter tube holders are provided by prior art patents. One example is a catheter tube holder which has two adhesive members connected by an adhesive narrow bridge to secure the members in a doubled over form when the two main members are used to position a catheter tube to a patient. Another example is catheter tube anchoring device system which has an adhesively-attachable single-piece having two channels connected by a bridge, each channel for receiving a tubular segment. However, what is needed is an adhesively-attachable H-shaped catheter tube anchoring device having two flexible side members and a rigid crossmember therebetween, the crossmember having a retainer mounted thereto for receiving a catheter tube and for holding the catheter tube at a 3-degree angle and further having two rigid vertically-oriented gripping tabs, one on each side of the retainer, to be gripped while advancing the catheter forward in piercing the vein with a needle, thus reducing the risk of contaminating the catheter, thereby reducing the risk of patient infection, while also making starting an I.V. easier and faster. The present catheter tube anchoring device addresses the foregoing needs by providing an adhesively-attachable H-shaped catheter tube anchoring device which two flexible side members and a rigid crossmember therebetween, the crossmember having a retainer mounted thereto for receiving a catheter tube and for holding the catheter tube at a 3-degree angle and further having two gripping tabs, one on each side of the retainer, assisting in the advancement of a catheter needle into a patient's vein and in the attachment of a catheter adaptor to I.V. tubing.

FIELD OF THE INVENTION

The present invention relates to support catheter tube anchoring devices and, more specifically, to an adhesive H-shaped catheter tube anchoring device to secure a catheter to a patient's skin, the device having two flexible side members and a rigid cross-member therebetween to which a retainer is mounted, the retainer adapted to removably receive and hold a catheter tube at a 3-degree angle, and to which two rigid vertically-oriented gripping tabs are secured, one each side of the retainer, which are adapted to grip while advancing a catheter needle into a patient's vein and while attaching a catheter adaptor to I.V. tubing, thereby increasing patient comfort, reducing the risk of contamination, and the risk of patient infection, as well as making the starting of an I.V. easier and faster.

SUMMARY OF THE INVENTION

The present catheter tube anchoring device is provided to securely anchor a catheter tube to a site on a patient's skin. The H-shaped device has adhesively-attachable two flexible side members and a rigid crossmember therebetween, the crossmember having a retainer mounted thereto for receiving a catheter adaptor and for holding the catheter adaptor at a 3-degree angle and further having two rigid gripping tabs, one on each side of the retainer, to be gripped while advancing the catheter needle forward in piercing the vein with a needle and while attaching the catheter adaptor to I.V. tubing, thus reducing the risk of contaminating the catheter adaptor and the catheter itself, increasing patient comfort, reducing the risk of patient infection, while also making starting an I.V. easier and faster. The side members and crossmember have an adhesive bottom surface, which is adapted to attach to a patient's skin, and a removable backing over the bottom surface. The adhesive bottom surface is divided into two L-shaped strips and two rectangular-shaped strips for easy the removal of the covering.

To use the present device, before insertion of the catheter, the hub of the catheter is snapped into the retainer by the user, such as a nurse or physician. Then, gripping one of the tabs on either side of the retainer, depending on the dominant hand of the user, the catheter is advanced forward after locating and piercing the vein with a needle. Using the tabs to advance the catheter reduces the risk of contaminating the catheter and giving the patient an infection because the user's gloved fingers would not come into direct contact with the hub of the catheter of the catheter itself. Conventionally, a user uses a thumbnail to push on a ridge of the hub of the catheter thereby making it very easy to contaminate the catheter by touching the catheter before it enters the vein, which may occur even more easily if the user has big thumbs. After the catheter is in place, the user simply holds one of the tabs while attaching the saline lock or I.V. tubing with the other hand. The side members and crossmember are then slightly lifted to remove the backing and then pressed down to secure the device to a patient's skin. This device is much less cumbersome than securing a catheter into place with tape, particularly when the nurse or physician is wearing gloves. In addition, the present device reduces a patient's pain when moving around because the catheter and I.V. do not pull at the side of the insertion point.

An alternative embodiment includes prism shaped tabs containing a pressure-release polymer adhesive-containing capsules which releases the polymer adhesive through mesh openings on the bottom side of the gripping tabs and onto an absorbent pad disposed on the entire bottom side of the crossmember and then onto a patient's skin to secure the device thereto either alone or in combination with a second adhesive previously applied to the patient's skin.

As such, the general purpose of the improved catheter tube anchoring device which has all of the advantages of the prior art mentioned heretofore and many novel features that result in an improved catheter tube anchoring device which is not anticipated, rendered obvious, suggested, or even implied by the prior art, either alone or in combination thereof.

An object of the present catheter tube anchoring device to reduce the risk of contamination of a catheter, thereby reducing the risk of patient infection.

Another object of the present catheter tube anchoring device is to make the starting of an I.V. much easier and faster than permitted by prior art devices.

Yet another object of the present catheter tube anchoring device is to easily secure a catheter to a patient's skin.

Still another object of the present device is to reduce pain accompanying IV insertion when a patient moves around.

Thus has been broadly outlined the more important features of the improved catheter tube anchoring device so that the detailed description thereof that follows may be better understood and in order that the present contribution to the art may be better appreciated.

DETAILED DESCRIPTION OF THE DRAWINGS

Figure 1:
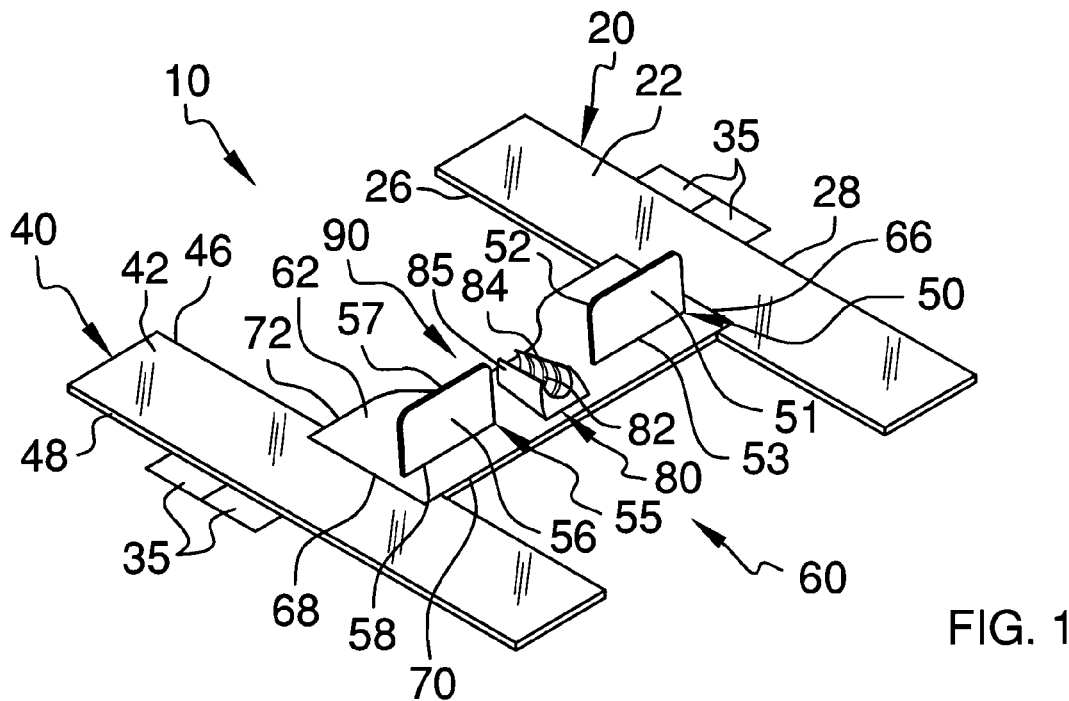
FIG. 1 is an isometric top view.

With reference now to the drawings, and in particular FIGS. 1 through 8 thereof, examples of the employing the principles and concepts of the present catheter tube anchoring device, generally designated by the reference number 10, will be described.

Referring to FIGS. 1 through 8, the present catheter tube anchoring device 10 is used to secure catheter tube to a patient. The present device 10 provides a flexible, rectangular first side member 20, a flexible, rectangular second side member 40 in closely-spaced, parallel relation to the first side member 20, and a rigid crossmember 60 therebetween thereby forming an H-shaped configuration. The first side member 20 has an upper portion 22, a lower portion 24, inner side 26, and an outer side 28. The second side member 40 has a top portion 42, a bottom portion 44, an inner edge 46, and an outer edge 48.

The generally rectangular crossmember 60 has top side 62, a bottom side 64, an outer first edge 66, an outer second edge 68, a front edge 70, and a rear edge 72. The outer first edge 66 is affixed to the center of the upper portion 22, near the inner side 26 of the first side member 20. The outer second edge 68 is affixed to the center of the top portion 42, near the inner edge 46 of the second side member 40.

A retainer 80 having a longitudinally disposed channel 82 therein is adapted to removably secure a catheter adaptor 100. The retainer 80 is mounted to the center of the top side 62 of the crossmember 60. The retainer 80 attached to a U-clip 89 holds a catheter adaptor 100 at a 3-degree angle 87 to increase patient comfort. The retainer 80 has a right side 84 and a left side 85. The position of the retainer 80 in the center of the top side 62 of the crossmember 60 balances the retainer 80 in correct position not only for patient comfort while moving around, but also for permitting easy removal of backing 30 from an adhesive layer 99 to secure the device 10 to a patient 200 without pulling on a needle 101 inserted in a patient's vein, thus further increasing patient comfort.

An indention 90 in the rear edge 72 of the crossmember 60 and adjacent to the retainer 80 is configured to allow a catheter adaptor 100 to be removably secured within the channel 82. The indention 90 increases the ease with which a catheter adaptor 100 is inserted into the retainer 80. Insertion of a catheter adaptor 100 in to the retainer 80 is easier with the presence of the indention 90 in the crossmember 60 than into a retainer 80 affixed to a crossmember 60 without the indention 90.

Figure 6:
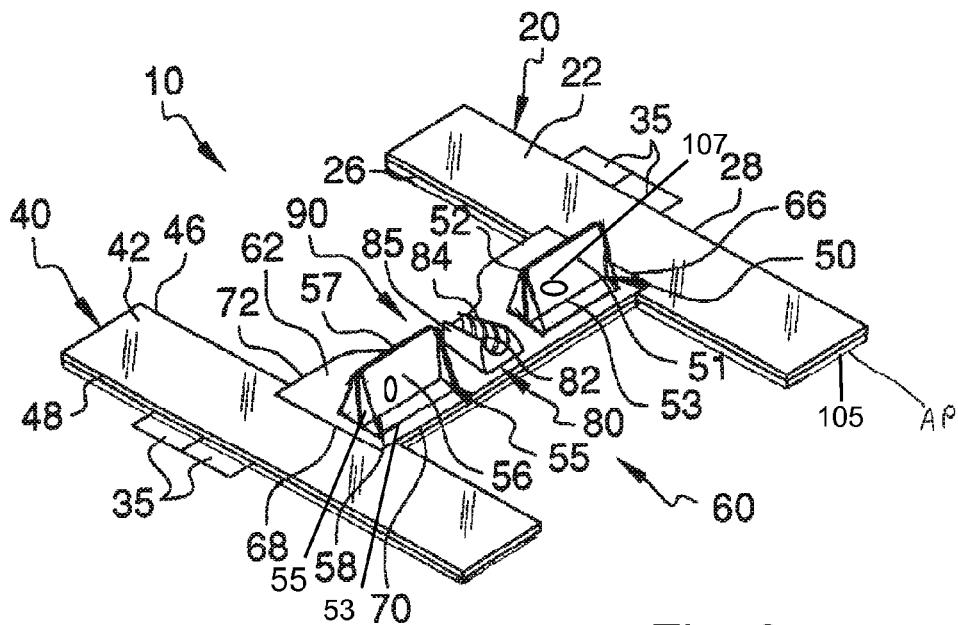
FIG. 6 is an isometric top view of an alternative embodiment.
Figure 7:
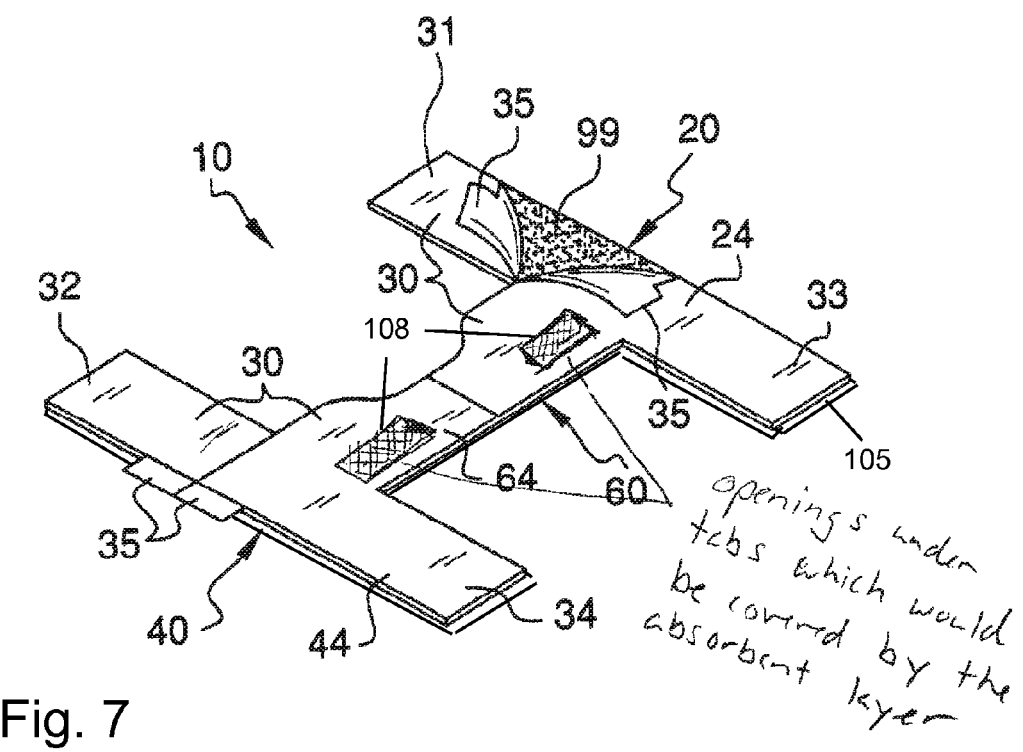
FIG. 7 is an isometric bottom view thereof.
Figure 8:
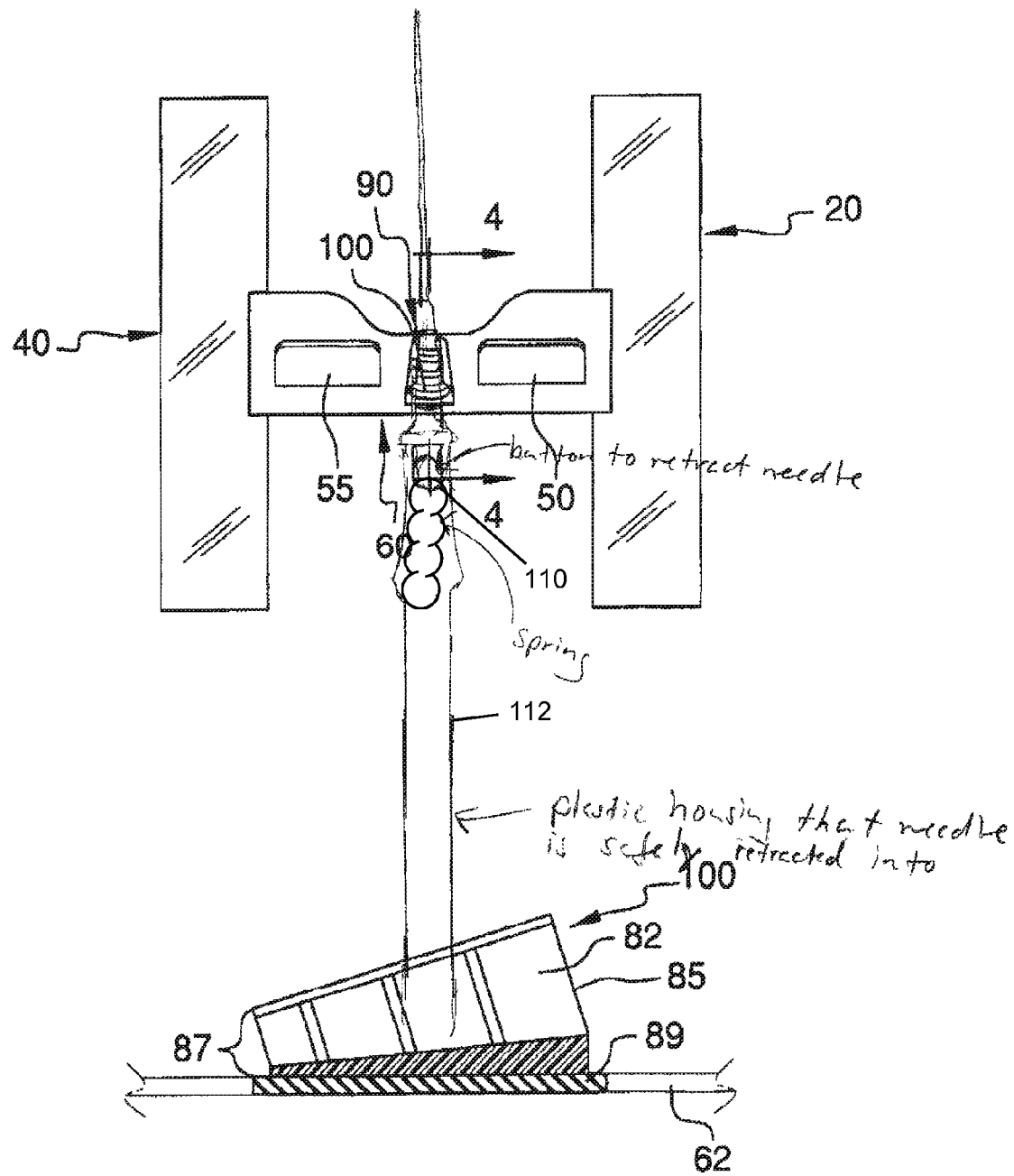
FIG. 8 is an in-use view thereof.

A rigid first gripping tab 50 is mounted to the top side 62 of the crossmember 60 in vertical relation thereto and between the retainer right side 84 and the outer first edge 66 of the crossmember 60. The first gripping tab 50 has a front side 51, a rear side 52 and a bottom edge 53. The bottom edge 53 is affixed to the top side 62 of the crossmember 60 in parallel position in relation to the front edge 70. A rigid second gripping tab 55 mounted to the top side 62 of the crossmember 60 in vertical relation thereto and between the retainer 80 left side 85 and the outer second edge 68 of the crossmember 60. The second gripping tab 55 has a front wall 56, a rear wall 57, and a lower edge 58. The lower edge 58 is affixed to the top side 62 of the crossmember 60 in parallel position in relation to the front edge 70. The gripping tabs 50, 55 are not a design choice, but rather are important to the functionality of the device 10. The gripping tabs reduce the risk of contaminating the catheter adaptor 100 by preventing direct contact of the user's fingers with the catheter adaptor 100 or catheter itself. Thus, the risk of infecting a patient 100 is reduced. The use of the gripping tabs 50, 55 for advancing the needle 101 into the patient's 200 vein reduces the likelihood of contamination and potential for patient infection. In another embodiment, each of the first gripping tab 50 and the second gripping tab 55 have a triangular prism shape which has the same footprint as the preferred embodiment first gripping tab 50 and the second gripping tab 55. In this embodiment each of the first gripping tab 50 and the second gripping tab 55 have an internal cavity 54 therein and a rectangular front side 51 perpendicular to the crossmember 60, as shown in FIG. 6. During use the front side 51 of each of the first and second gripping tabs 50, 55 faces the user.

Figure 2:
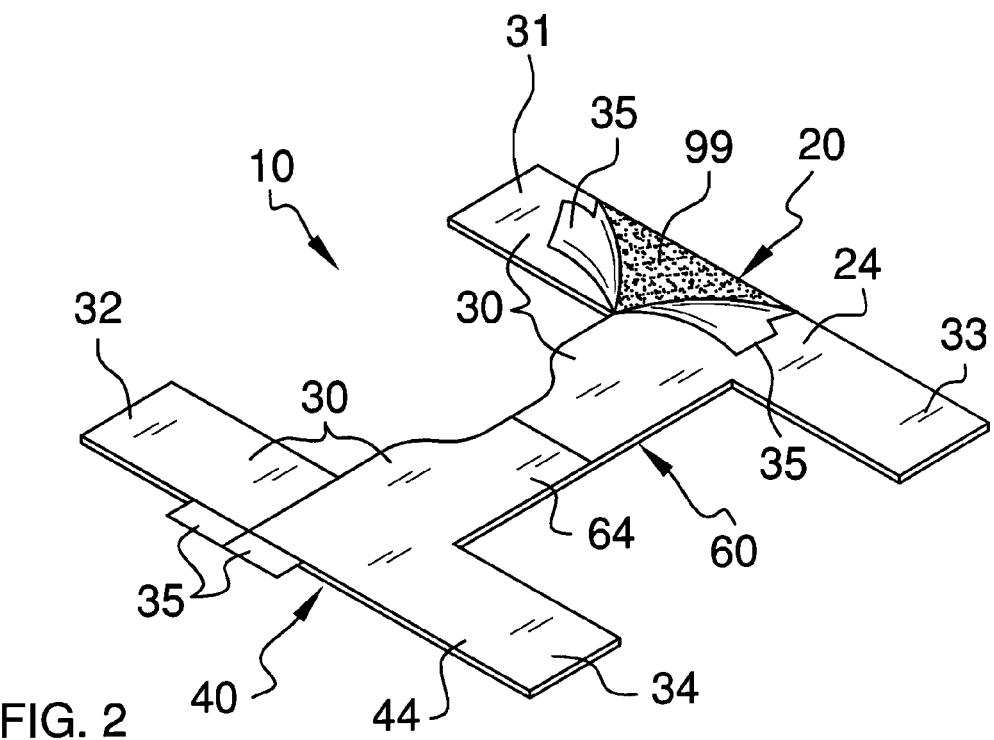
FIG. 2 is an isometric bottom view.
Figure 3:
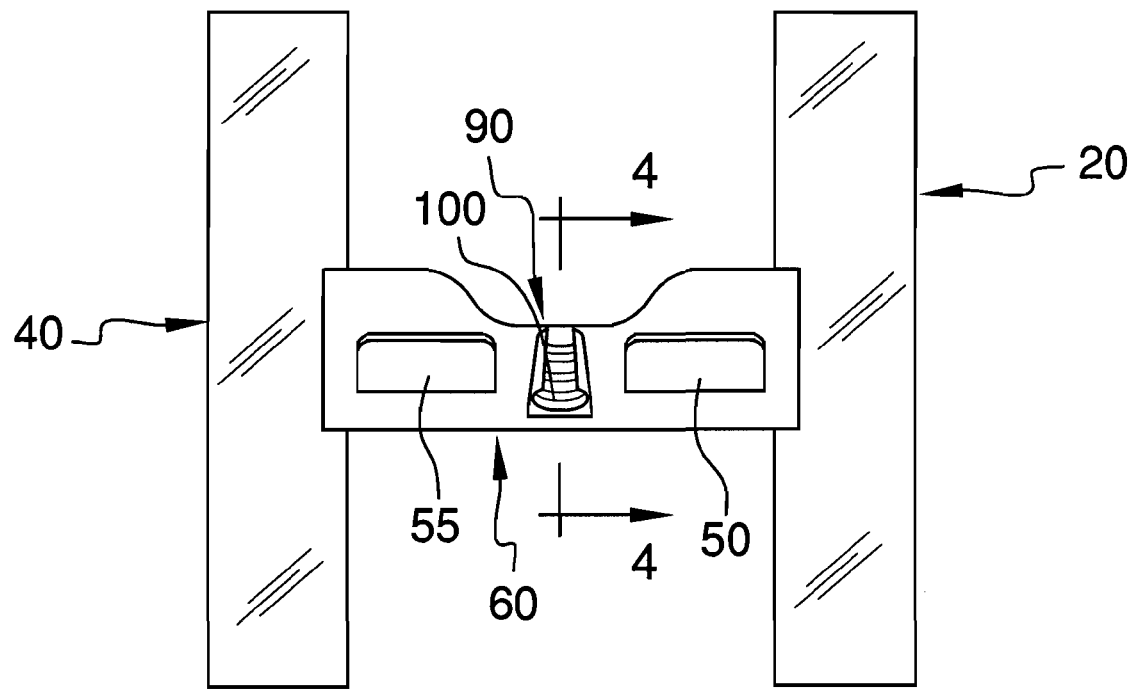
FIG. 3 is a top plan view.
Figure 4:
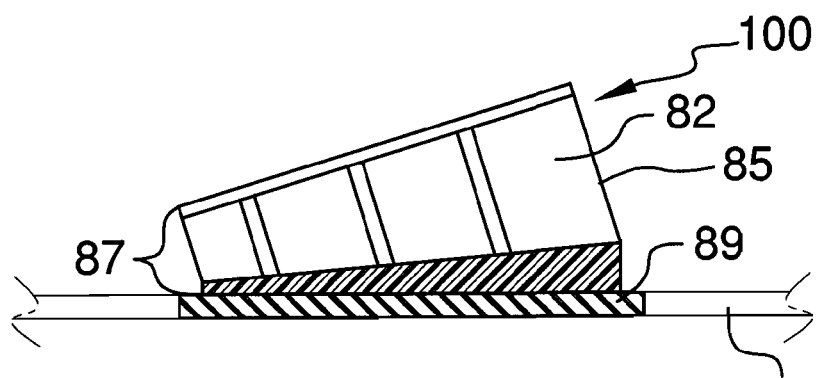
FIG. 4 is a cross-section view taken along line 4-4 of FIG. 3.
Figure 5:
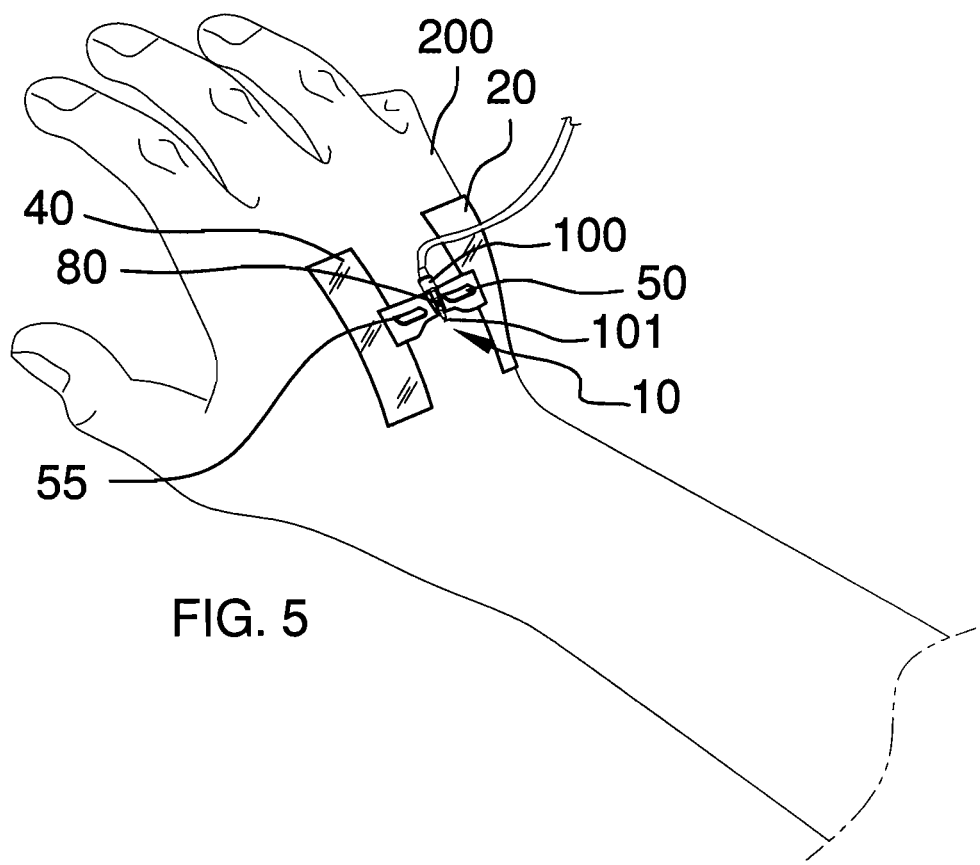
FIG. 5 is an isometric in-use view.

An adhesive layer 99, shown in FIG. 2, is disposed on the lower portion 24 of the first side member 20, on the bottom portion 44 of the second side member 40, and on the bottom side 64 of the crossmember 60, permits the device 10 to be secured to a patient's skin more easily than securement with tape. In the alternative embodiment, an absorbent pad 105, which is disposed on the entire bottom side 64 of the crossmember 60, the first side member 20 and the second side member 40, is substituted for the adhesive layer 99. Further, in the alternative embodiment, a pressure-released polymer adhesive-containing capsule 107 is disposed within the internal cavity 54 of each of the first and second gripping tabs 50, 55. Each of the capsules 107 has a diameter of approximately ⅛ inch. In use, when securing the alternative embodiment of the device 10 to the patient, the user places pressure on the first and second gripping tabs 50, 55 to break open the capsules 107 therein and to release the polymer adhesive which passes through mesh openings 108 disposed on an bottom edge 53 of each of the first and second gripping tabs 50, 55 to permeate the absorbent pad and then onto user's skin to adhere the device 10 onto the patient's skin. Alternatively, the polymer adhesive is released onto and through the absorbent pad 105 onto the patient's skin and then combines with a second adhesive which has already been applied to the patient's skin, prior to the polymer adhesive, and the combination thereof secures the device 10 onto the patient's skin.

A backing 30, which removably covers the adhesive layer 99 has a rectangular first part 31, a rectangular second part 32, a L-shaped third part 33, and a L-shaped fourth part 34. The first part 31, second part 32, third part 33, and fourth part 34, each having a backing removal extension piece 35. In the alternative embodiment, the backing 30 removably covers the absorbent pad 105.

A spring-loaded push-release button 110 is disposed atop an attachment end of a plastic housing 112 into which the needle is retracted.

Operation:

To use the present device 10, a user, such as a nurse or physician, begins by snapping a catheter adaptor 100 into the retainer 80 before inserting a needle 101 into a patient. The user then proceeds by locating and piercing the patient's 200 vein with a needle 101 of the catheter adaptor 100. Then, gripping either he first gripping tab 50 or second gripping tab 55 prior to advancing the needle 101 into the patient 200, a user advances the needle 101 into a patient's 200 vein. After the needle is in place in the vein, the user holds onto to either the first gripping tab 50 or second gripping tab 55, depending on the user's dominant hand, while attaching corresponding I.V. tubing with the user's other hand.

To secure the device 10 to the patient's skin, the user slightly lifts the crossmember 60 while removing the backing 30 by pulling on a corresponding extension piece 35, slightly lifts either the first side member 20 or second side member 40 while removing said backing 30 by pulling on a corresponding extension piece 35. After removing the backing 30, the user presses down on the crossmember 60, first side member 20, and second side member 40 to secure the device 10 to a patient 200.

Use of the alternative embodiment is the same, except to secure the device 10 to the patient's skin, the user slightly lifts the crossmember 60 while removing the backing 30 from the lower side 109 of the absorbent pad 105 by pulling on a corresponding extension piece. The user then places pressure on the first and second gripping tabs 50, 55 to break open the capsules 107 and to release the polymer adhesive through the mesh openings 108 to permeate the absorbent pad, and then onto to the user's skin to adhere the device 10 onto the patient's skin. Alternatively, the polymer adhesive is released onto and through the absorbent pad 105 onto the patient's skin and then combines with a second adhesive which has already been applied to the patient's skin, prior to the polymer adhesive, and the combination thereof secures the device 10 onto the patient's skin. To retract the needle, the user pushes the spring-loaded push-release button 110 disposed atop an attachment end of the plastic housing 112.

What is claimed is:

1. An H-shaped catheter tube anchoring device for securing a catheter tube to a patient comprising:
    a flexible, rectangular first side member having an upper portion, a lower portion, inner side, and an outer side;
    a flexible, rectangular second side member having a top portion, a bottom portion, an inner edge, and an outer edge, said side members adapted to be secured to the skin of a patient in closely-spaced, parallel relation;
    a rigid crossmember having top side, a bottom side, an outer first edge, an outer second edge, a front edge, and a rear edge, said outer first edge affixed to the center of the upper portion, near the inner side of said first side member and said second edge affixed to the center of the top portion, near the inner edge of said second side member, wherein the crossmember is more rigid than each of the first side member and the second side member;
    a retainer having a longitudinally disposed channel therein adapted to removably secure a catheter adaptor, said retainer mounted to the center of the top side of said crossmember;
    an indention in the rear edge of said crossmember and adjacent to said retainer, said indention configured to allow a catheter adaptor to be removably secured within said channel;
    a rigid first gripping tab mounted to the top side of said crossmember in vertical relation thereto and between said retainer right side and the first edge of said crossmember, said first gripping tab having a front side, a rear side, and a bottom edge, the bottom edge affixed to the top side of the crossmember in parallel position in relation to the front edge, wherein the first gripping tab is as rigid as the crossmember;
    a rigid second gripping tab mounted to the top side of said crossmember in vertical relation thereto and between said retainer left side and the second edge of said crossmember, said second gripping tab having a front wall, a rear wall and a lower edge, said lower edge affixed to the top side of the crossmember in parallel position in relation to the front edge, wherein the second gripping tab is as rigid as the crossmember;
    an adhesive layer on the lower portion of said first side member, on the bottom portion of said second side member, and on said crossmember;
    a backing removably covering said adhesive layer comprising:
        a rectangular first part,
        a rectangular second part,
        a L-shaped third part, and
        a L-shaped fourth part, said first part, second part, third part and fourth part having a backing removal extension piece.

2. The catheter tube anchoring device of claim 1 wherein said channel removably secures said catheter adaptor at approximately a 3-degree angle.

3. An H-shaped catheter tube anchoring device for securing a catheter tube to a patient comprising:
    a flexible, rectangular first side member having an upper portion, a lower portion, inner side, and an outer side;
    a flexible, rectangular second side member having a top portion, a bottom portion, an inner edge, and an outer edge, said side members adapted to be secured to the skin of a patient in closely-spaced, parallel relation;
    a rigid crossmember having top side, a bottom side, an outer first edge, an outer second edge, a front edge, and a rear edge, said outer first edge affixed to the center of the upper portion, near the inner side of said first side member and said second edge affixed to the center of the top portion, near the inner edge of said second side member, wherein the crossmember is more rigid than each of the first side member and the second side member;
    a retainer having a longitudinally disposed channel therein adapted to removably secure a catheter adaptor, said retainer mounted to the center of the top side of said crossmember;
    an indention in the rear edge of said crossmember and adjacent to said retainer, said indention configured to allow a catheter adaptor to be removably secured within said channel;
    a rigid prism-shaped first gripping tab mounted to the top side of said crossmember in vertical relation thereto and between said retainer right side and the first edge of said crossmember, said first gripping tab having a front side, a rear side, and a bottom edge, the bottom edge affixed to the top side of the crossmember in parallel position in relation to the front edge, wherein the first gripping tab is as rigid as the crossmember;
    a rigid prism-shaped second gripping tab mounted to the top side of said crossmember in vertical relation thereto and between said retainer left side and the second edge of said crossmember, said second gripping tab having a front wall, a rear wall and a lower edge, said lower edge affixed to the top side of the crossmember in parallel position in relation to the front edge, wherein the second gripping tab is as rigid as the crossmember;
    wherein each of the first gripping tab and the second gripping tab have an internal cavity therein and a rectangular front side perpendicular to the crossmember;
    an absorbent pad disposed on the entire bottom side of the crossmember and the first side member and the second side member, the absorbent pad having a lower side;
    a plurality of spaced apart mesh openings disposed within the bottom edge of each of the first gripping tab and the second gripping tab, wherein the mesh openings are disposed between the first and second gripping tabs and the absorbent pad;

a pressure-released polymer adhesive-containing capsule disposed within the internal cavity of each of the first and second gripping tabs, wherein each of the capsules has a diameter of approximately ⅛ inch;

wherein upon placement of pressure upon the capsules releases the polymer adhesive contained within each of the capsules through the mesh openings;

wherein upon release of the polymer adhesive, the polymer adhesive permeates the absorbent pad;

wherein upon permeation of the absorbent pad with the polymer adhesive, the polymer adhesive passes onto a patient's skin, whereby the first side member, the second side member and the crossmember are secured to a patient's skin;

a backing removably covering said absorbent pad, the backing comprising:
a rectangular first part,
a rectangular second part,
a L-shaped third part, and
a L-shaped fourth part, said first part, second part, third part and fourth part having a backing removal extension piece.

4. An H-shaped catheter tube anchoring device for securing a catheter tube to a patient comprising:

a flexible, rectangular first side member having an upper portion, a lower portion, inner side, and an outer side;

a flexible, rectangular second side member having a top portion, a bottom portion, an inner edge, and an outer edge, said side members adapted to be secured to the skin of a patient in closely-spaced, parallel relation;

a rigid crossmember having top side, a bottom side, an outer first edge, an outer second edge, a front edge, and a rear edge, said outer first edge affixed to the center of the upper portion, near the inner side of said first side member and said second edge affixed to the center of the top portion, near the inner edge of said second side member, wherein the crossmember is more rigid than each of the first side member and the second side member;

a retainer having a longitudinally disposed channel therein adapted to removably secure a catheter adaptor, said retainer mounted to the center of the top side of said crossmember;

an indention in the rear edge of said crossmember and adjacent to said retainer, said indention configured to allow a catheter adaptor to be removably secured within said channel;

a rigid prism-shaped first gripping tab mounted to the top side of said crossmember in vertical relation thereto and between said retainer right side and the first edge of said crossmember, said first gripping tab having a front side, a rear side, and a bottom edge, the bottom edge affixed to the top side of the crossmember in parallel position in relation to the front edge, wherein the first gripping tab is as rigid as the crossmember;

a rigid prism-shaped second gripping tab mounted to the top side of said crossmember in vertical relation thereto and between said retainer left side and the second edge of said crossmember, said second gripping tab having a front wall, a rear wall and a lower edge, said lower edge affixed to the top side of the crossmember in parallel position in relation to the front edge, wherein the second gripping tab is as rigid as the crossmember;

wherein each of the first gripping tab and the second gripping tab have an internal cavity therein and a rectangular front side perpendicular to the crossmember;

an absorbent pad disposed on the entire bottom side of the crossmember directly below each of the first and second gripping tabs, the absorbent pad having a lower side;

a plurality of spaced apart mesh openings disposed within the bottom edge of each of the first gripping tab and the second gripping tab, wherein the mesh openings are disposed between the first and second gripping tabs and the absorbent pad;

a pressure-released polymer adhesive-containing capsule disposed within the internal cavity of each of the first and second gripping tabs, wherein each of the capsules has a diameter of approximately ⅛ inch;

wherein upon placement of pressure upon the capsules releases the polymer adhesive contained within each of the capsules through the mesh openings;

wherein upon release of the polymer adhesive through the mesh openings, the polymer adhesive permeates the absorbent pad;

wherein upon permeation of the absorbent pad with the polymer adhesive, the polymer adhesive passes onto a patient's skin, wherein the polymer adhesive combines with a second adhesive disposed on a patient's skin, whereby the first side member, the second side member and the crossmember are secured to a patient's skin;

a backing removably covering said absorbent pad, the backing comprising:
a rectangular first part,
a rectangular second part,
a L-shaped third part, and
a L-shaped fourth part, said first part, second part, third part and fourth part having a backing removal extension piece.

5. A catheter tube anchoring device for securing a catheter tube to a patient comprising:

an elongated first side member having an upper portion, a lower portion, inner side, and an outer side;

an elongated second side member having a top portion, a bottom portion, an inner edge, and an outer edge, a crossmember having top side, a bottom side, an outer first edge, an outer second edge, a front edge, and a rear edge, said outer first edge being connected to the upper portion of said first side member and said second edge being connected to the top portion of said second side member such that said crossmember, said first side member and said second side member have a generally H-shaped configuration, wherein the crossmember is relatively more rigid than each of the first side member and the second side member;

a retainer having a channel formed therein to removably receive a catheter adaptor, said retainer being positioned on the top side of said crossmember, the channel having a longitudinal axis along which the catheter adapter is inserted into the retainer;

a first gripping tab mounted to the top side of said crossmember and extending substantially perpendicular to the top side of the crossmember, said first gripping tab being positioned between said retainer and the outer side of said first side member;

a second gripping tab mounted to the top side of said crossmember and extending substantially perpendicular to the top side of the crossmember , said first gripping tab being positioned between said retainer and the outer edge of said second side member;

an adhesive layer on the lower portion of said first side member, on the bottom portion of said second side member; and a removable backing covering said adhesive layer.

6. The catheter tube anchoring device of claim 5 further including an indention in the rear edge of said crossmember and being located adjacent to said retainer.

7. The catheter tube anchoring device of claim 5 wherein the adhesive layer is on the bottom side of said crossmember.

8. The catheter tube anchoring device of claim 5 wherein the removable backing comprises:
   a rectangular first part,
   a rectangular second part,
   a L-shaped third part, and
   a L-shaped fourth part,
   wherein said first part, second part, third part and fourth part have a backing removal extension piece 9. A catheter tube anchoring device for securing a catheter tube to a patient comprising:
   an elongated first side member;
   an elongated second side member extending in a spaced and generally parallel relationship to the first side member;
   a crossmember extending between and being connected to the first and second side members such that the crossmember, the first side member and the second side member have a generally H-shaped configuration, the cross member having a top side;
   a retainer on the top side of the crossmember and having a channel formed therein to removably receive a catheter adaptor, the retainer being positioned on the top side of the crossmember, the channel having a longitudinal axis along which the catheter adapter is inserted into the retainer;
   a first gripping tab mounted to the top side of said crossmember and extending substantially perpendicular to the top side of the crossmember, at least a portion of the first gripping tab being positioned between the retainer and the first side member;
   a second gripping tab mounted to the top side of said crossmember and extending substantially perpendicular to the top side of the crossmember, at least a portion of the first gripping tab being positioned between the retainer and the second side member; and
   an adhesive layer on a lower surface of the first side member and a lower surface of the second side member for adhering to the patient.

10. The catheter tube anchoring device of claim 9 wherein the first gripping tab and the second gripping tab are oriented in a plane substantially perpendicular to the longitudinal axis of the channel of the receiver.

11. The catheter tube anchoring device of claim 9 wherein the first and second side members are elongated along axes substantially parallel to the longitudinal axis of the channel of the retainer.

12. The catheter tube anchoring device of claim 9 wherein the crossmember is relatively more rigid than each of the first side member and the second side member.

13. The catheter tube anchoring device of claim 9 further including an indention located in a rear edge of the crossmember adjacent to the retainer.

14. The catheter tube anchoring device of claim 9 wherein the adhesive layer is on the bottom side of the crossmember.

15. The catheter tube anchoring device of claim 9 additionally comprising a removable backing covering the adhesive layer on the lower surfaces of the side members.

16. The catheter tube anchoring device of claim 15 wherein the removable backing comprises multiple pieces.

\* \* \* \* \*